United States Patent
Abe et al.

(10) Patent No.: US 7,140,893 B2
(45) Date of Patent: Nov. 28, 2006

(54) LIGHT SOURCE DEVICE FOR MEDICAL ENDOSCOPE

(75) Inventors: Kazunori Abe, Saitama (JP); Daisuke Ayame, Saitama (JP)

(73) Assignee: Fujinon Corporation, Saitama (JP)

( * ) Notice: Subject to any disclaimer, the term of this patent is extended or adjusted under 35 U.S.C. 154(b) by 189 days.

(21) Appl. No.: 10/782,840

(22) Filed: Feb. 23, 2004

(65) Prior Publication Data
US 2004/0165393 A1   Aug. 26, 2004

(30) Foreign Application Priority Data
Feb. 24, 2003   (JP)   ............................. 2003-046184

(51) Int. Cl.
*H01R 13/44* (2006.01)
(52) U.S. Cl. ..................... 439/144; 362/155; 439/188; 439/157; 439/487; 439/700; 439/923; 439/181
(58) Field of Classification Search ................ 439/181, 439/911, 142, 144, 700, 824, 188, 157, 487, 439/923; 362/373–375, 94, 362, 155, 263, 362/802; 200/51.1
See application file for complete search history.

(56) References Cited

U.S. PATENT DOCUMENTS

| | | | | |
|---|---|---|---|---|
| 1,995,172 A | * | 3/1935 | Douglas | 439/700 |
| 2,724,096 A | * | 11/1955 | Klostermann | 439/824 |
| 3,642,361 A | * | 2/1972 | Streu | 353/57 |
| 4,195,331 A | * | 3/1980 | Jones | 362/368 |
| 4,887,154 A | * | 12/1989 | Wawro et al. | 348/68 |
| 5,417,595 A | * | 5/1995 | Cullen et al. | 439/700 |
| 5,526,249 A | * | 6/1996 | Karasawa et al. | 362/362 |
| 5,924,791 A | * | 7/1999 | Arai et al. | 362/373 |
| 6,179,446 B1 | * | 1/2001 | Sarmadi | 362/264 |
| 6,676,277 B1 | * | 1/2004 | Gordin | 362/263 |
| 6,910,911 B1 | * | 6/2005 | Mellott et al. | 439/358 |

FOREIGN PATENT DOCUMENTS

| | | |
|---|---|---|
| JP | 6-067097 | 3/1994 |
| JP | 9-327435 | 12/1997 |

* cited by examiner

*Primary Examiner*—Neil Abrams
(74) *Attorney, Agent, or Firm*—Young & Thompson

(57) ABSTRACT

A light source device for a medical endoscope system comprises a lamp unit including a xenon lamp and a heat sink, with fins, certain ones of which form electrodes, a lamp housing into which the lamp unit is removably which is provided with first power electrodes and discharge electrodes of a static discharge circuit. These first power electrodes and discharge electrodes are biased in a direction of removal of the lamp unit. The first power electrodes are brought into contact with the heat sink electrodes and thrust back by the heat sink when the lamp unit is set in the lamp housing. The discharge electrodes are thrust back away from the discharge circuit by the heat sink on the way of insertion of the lamp unit into the lamp housing and allowed to return to electric coupling to the discharge circuit ground on the way of removal of the lamp unit from the lamp housing. A pivot door may be used and includes pin for blocking door closure if the lamp unit is not properly inserted and also includes a switch interlock for effecting power to the lamp unit. Rotational inserting/ejecting levers may also be used.

16 Claims, 11 Drawing Sheets

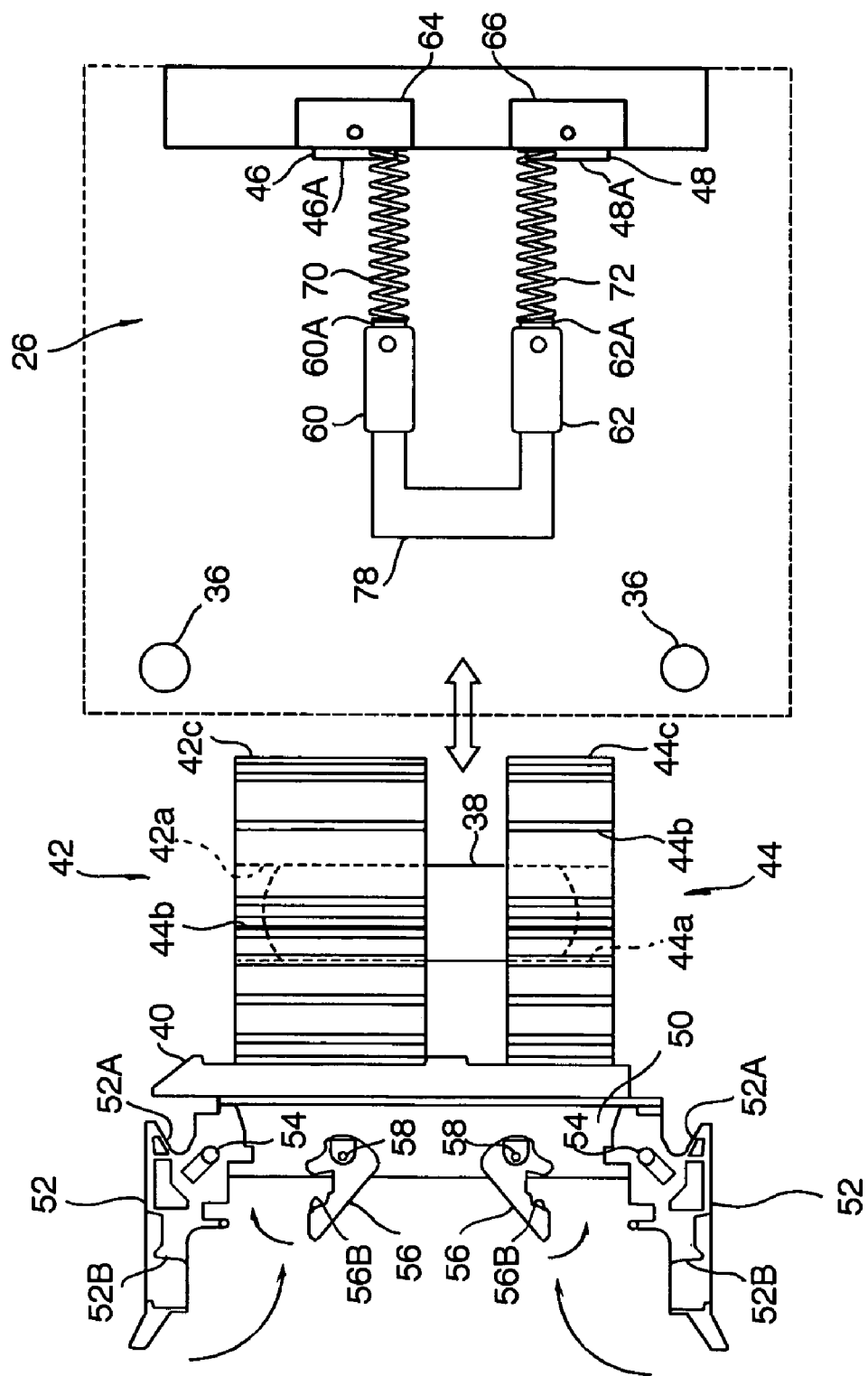

LIGHT SOURCE DEVICE FOR MEDICAL ENDOSCOPE

BACKGROUND OF THE INVENTION

1. Field of the Invention

The present invention relates to a light source device for providing illumination light to an endoscope system, in particular, a medical endoscope system.

2. Description of Related Art

A light source device for use with a medical endoscope system is detachably connected to an endoscope to supply illumination light to a body cavity through a light guide. The light source device generally has a lamp unit including an electric lamp, a lamp housing in which the lamp unit is removably installed, and an outer case in which the lamp housing is fixedly encased. The outer case is provided with an access door for opening and closing an access opening of the outer case to the lamp unit for periodic and temporary replacement of lamps. Periodic replacement of lamps is made at regular time intervals for the purpose of keep the light source device supplying a stable amount of illumination light.

One of light source devices for medical endoscope systems disclosed in, for example, Japanese Unexamined Patent Publication No. 6-67097 has a case provided with double access doors, namely an outer and an inner access door, for opening and closing an access opening of the case for an access to an electric lamp located far back from the access doors. The electric lamp is mounted to a heat sink fixedly installed in the case by means of fixing knobs. The inner access door serves as an interlock door to brake or open a lighting circuit for the electric lamp when it is opened or removed from the case.

Another light source device for medical endoscope systems disclosed in, for example, Japanese Unexamined Patent Publication No. 9-327435, has a case provided with an access door for opening and closing an access opening of the case for an access to an electric lamp mounted to a heat sink. The access door serves as a switch to bring a discharge circuit for discharging static electricity of the heat sink alive when it is opened or removed. The light source device ensures safety lamp replacement works because static electricity of the heat sink are discharged whenever the access door is opened or removed.

The light source device provided with double access doors has the problem that replacement of lamps involves opening and closing the double access doors and handling the fixing knobs to detach and fix the heat sink which are quite troublesome.

Further, in the prior art light source devices described above have the problem that the operator incurs a danger upon replacing lamps immediately after the service of the light source device because the heat sink is too hot to be set aside from the case.

SUMMARY OF THE INVENTION

It is therefore an object of the present invention to provide a light source device for a medical endoscope system that enables easy and safe lamp replacement works.

According to an aspect of the present invention, the foregoing object is accomplished by a light source device for supplying illumination light to an endoscope system that has a light source unit housing and a light source unit including an electric lamp, the electric lamp being electrically connected to a power source when the light source unit is inserted into the light source unit housing and disconnected from the power source when the light source unit is removed from the light source unit housing. The light source device comprises first power electrodes for transmitting electric power to the light source unit that are held for sliding movement in opposite directions for insertion and removal of the light source unit by the light source unit housing, second power electrodes for supplying electric power to the electric lamp which are fixedly attached to the light source unit, and biasing means incorporated in the light source unit housing for biasing the first power electrodes in the direction for removal of the light source unit. In the light source device, when the light source unit is inserted into the light source unit housing, the second power electrodes come to contact with and thrust back the first power electrodes against the biasing means, thereby electrically connecting the electric lamp to the power source.

The light source device thus structured keeps the second power electrodes of the light source unit reliably contacting with the first power electrodes of the light source unit housing under repulsion of the biasing springs when the light source unit is inserted in the light source unit housing in the right place. On the other hand, the light source unit is removed from the light source unit housing in a breeze with the assistance of the biasing springs.

According to another aspect of the present invention, the foregoing object is accomplished by a light source device for supplying illumination light to an endoscope system that has a light source unit housing and a light source unit including an electric lamp removably inserted into the light source unit housing. The light source device comprises a discharge circuit incorporated in the light source unit housing that operates to discharge static electricity of a charge built-up portion of the light source unit when electrically connected to the light source unit, sliding electrodes forming part of the discharge circuit and held for slide movement in opposite directions for insertion and removal of the light source unit by the light source unit housing, and biasing means for biasing the sliding electrodes in the direction for removal of the light source unit so as thereby to keep the sliding electrodes being electrically connected to the discharge circuit. In the light source device, the light source unit forces the sliding electrodes against the biasing means through engagement between the light source unit and the sliding electrodes so as to electrically disconnect the sliding electrodes from the discharge circuit following movement of the light source unit in the direction for insertion into the light source unit housing. Further, the light source unit allows the sliding electrodes to slide following movement of the light source unit in the direction for removal from the light source unit housing keeping in contact with the light source unit and then to be brought into electric connection with the discharge circuit, thereby discharging static electricity of the light source unit.

The light source device thus structured reliably brings the sliding electrodes into connection with the discharge circuit under repulsion of the biasing springs in the course of removing the light source unit from the light source unit housing, thereby discharging static electricity build up in the light source unit with the consequence that the light source unit is safely removed from the light source unit housing. Furthermore, the light source unit is removed from the light source unit housing in a breeze with the assistance of the biasing springs.

According to still another aspect of the present invention, the foregoing object is accomplished by a light source device for supplying illumination light to an endoscope system that has a light source unit housing and a light source unit including an electric lamp removably inserted into the light source unit housing. The light source unit comprises grip means for being gripped to hold the light source unit, a heat sink for holding the electric lamp, and insulating means of a material that is electrically nonconductive and low in thermal conductivity disposed between the grip means and the heat sink for thermally and electrically insulating the grip means from the heat sink.

The insulating means prevents the grip means from being influenced by heat of the heat sink. Therefore, the light source unit can be safely removed from the light source unit housing even when the heat sink is too hot to be handled immediately after the service of the light source device. Furthermore, the operator is prevented from incurring an electric shock upon gripping the grip means even when the heat sink is charged substantially.

According to a further aspect of the present invention, the foregoing object is accomplished by a light source device for supplying illumination light to an endoscope system that has a light source unit housing and a light source unit including an electric lamp removably inserted into the light source unit housing. The light source device has an access door for opening and closing an access opening of an outer case for an access to the light source unit and a projection provided on an inner side of the access door. The projection such as a pin strikes on the light source unit so as to prevent the access door from closing when the light source unit is incompletely inserted in the light source unit housing.

The light source device obviates an occurrence of wrong insertion of the light source unit into the light source unit housing.

BRIEF DESCRIPTION OF THE DRAWINGS

The above and other objects and features of the present invention will be clearly understood from the following detailed description when read with reference to the accompanying drawings, wherein the same numeral numbers have been used to denote same or similar parts or mechanisms throughout the drawings and in which:

FIG. 6 is a plan view of the light source unit housing and the light source unit before insertion into or after removal from the light source unit housing;

DETAILED DESCRIPTION OF THE PREFERRED EMBODIMENT

In the following description, parts which are not of direct importance to the invention and parts which are purely of conventional construction will not be described in detail. For example, details of the power supply circuit, the lighting circuit, the light guide means, the connector, etc. which are necessary to the light source unit, will not be set out in detail since their construction and operation can be easily arrived at by those skilled in the art.

Figure 1:
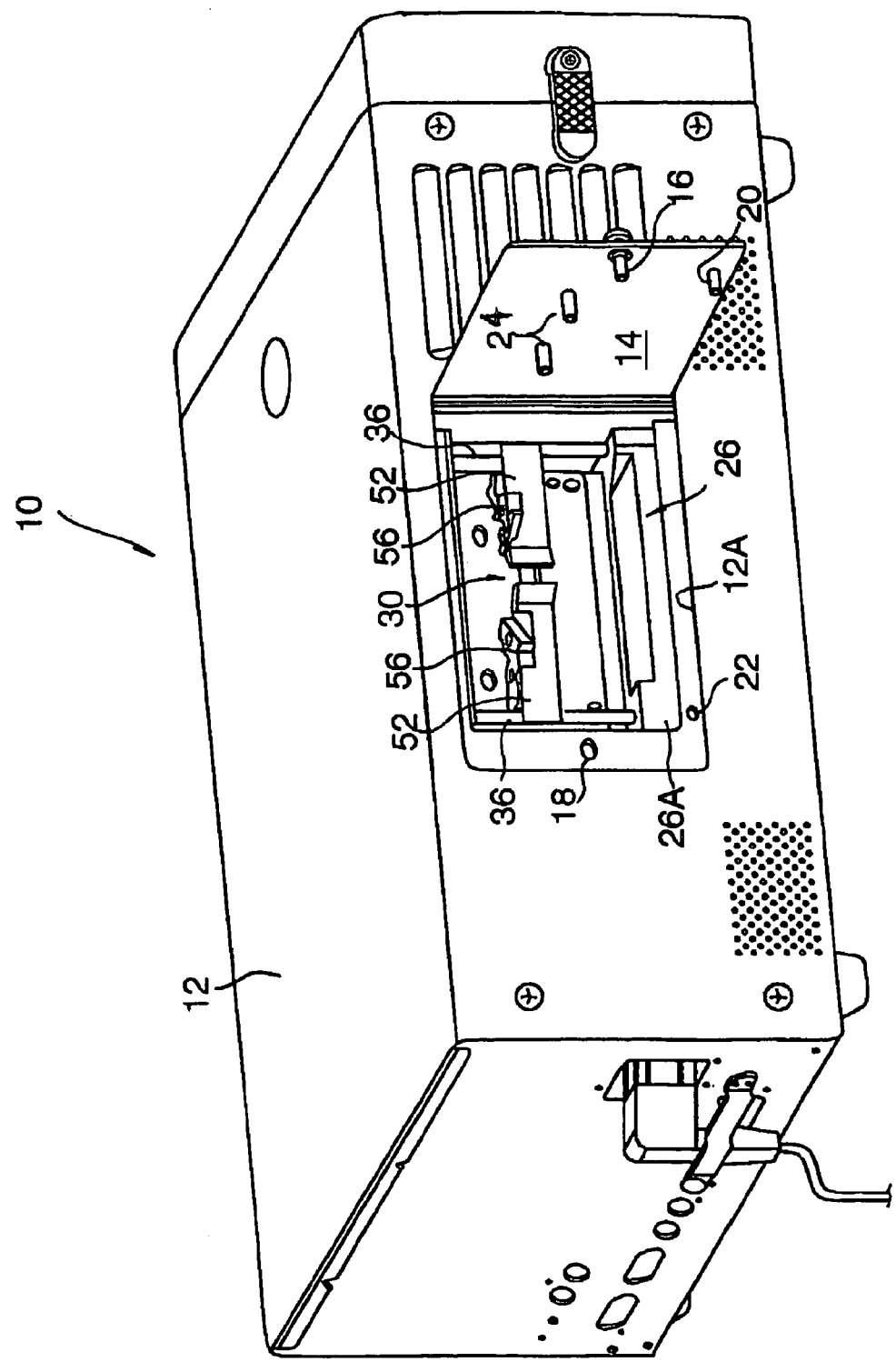
FIG. 1 is a perspective outline view of a light source device according to an embodiment of the present invention.
Figure 2:
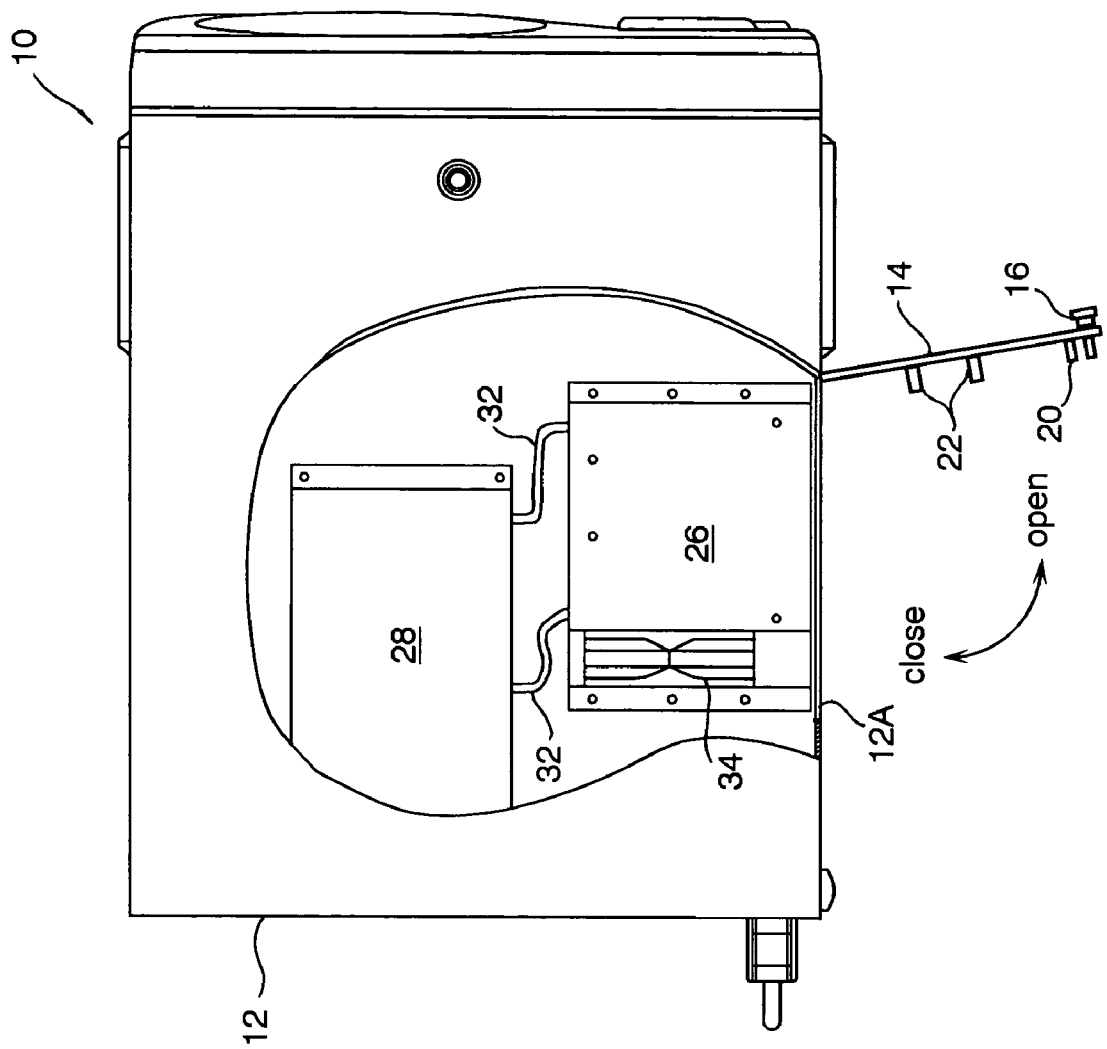
FIG. 2 is a plane view of the light source device partly cutaway.

Referring to the drawings in detail, and, in particular, to FIGS. 1 and 2 showing a light source device 10 for endoscopes according to an embodiment of the present invention, the light source device 10 has a generally rectangular box-shaped case 12 provided with a door 14 for opening and closing an access opening 12A. The door 14 is provided with a lock screw 16 that is tightened in a screw hole 18 of the case 12 to lock the door 14. The door 14 is further provided with interlock release means such as a pin 20 close to the lock screw 16 and a pair of safety means such as pins 24 at the center. The interlock release pin 20 is lead into a bore 22 formed in the case 12 to provide electrical interlock between a xenon lamp 38 incorporated in a light source unit 30 (see FIG. 3) and a power source (not shown) when the door 14 is closed and gets away from the bore 22 to disconnect the xenon lamp 38 from the power source when the door 14 is opened. The safety pins 24 are brought into a strike on parts of the light source unit 30 in a false position when the door 14 is closed.

As shown in FIG. 2, there are installed in the case 12 a stationary light source unit housing 26 in which the light source unit 30 is detachably mounted, a lighting control unit 28 including a constant current circuit and an on/off switch, and a cooling fan 34. These light source unit housing 26 and lighting unit 28, more specifically, the lamp and the constant current circuit, are electrically connected through cables 32. The cooling fan 26 is disposed adjacent to the light source unit housing to cool the interior of the light source unit housing 26. The light source unit housing 26 faces the access opening 12A of the case 12. The light source unit 30 shown in FIGS. 3 through 6 is inserted into and removable from the light source unit housing 26 through the access opening 12A.

Figure 3:
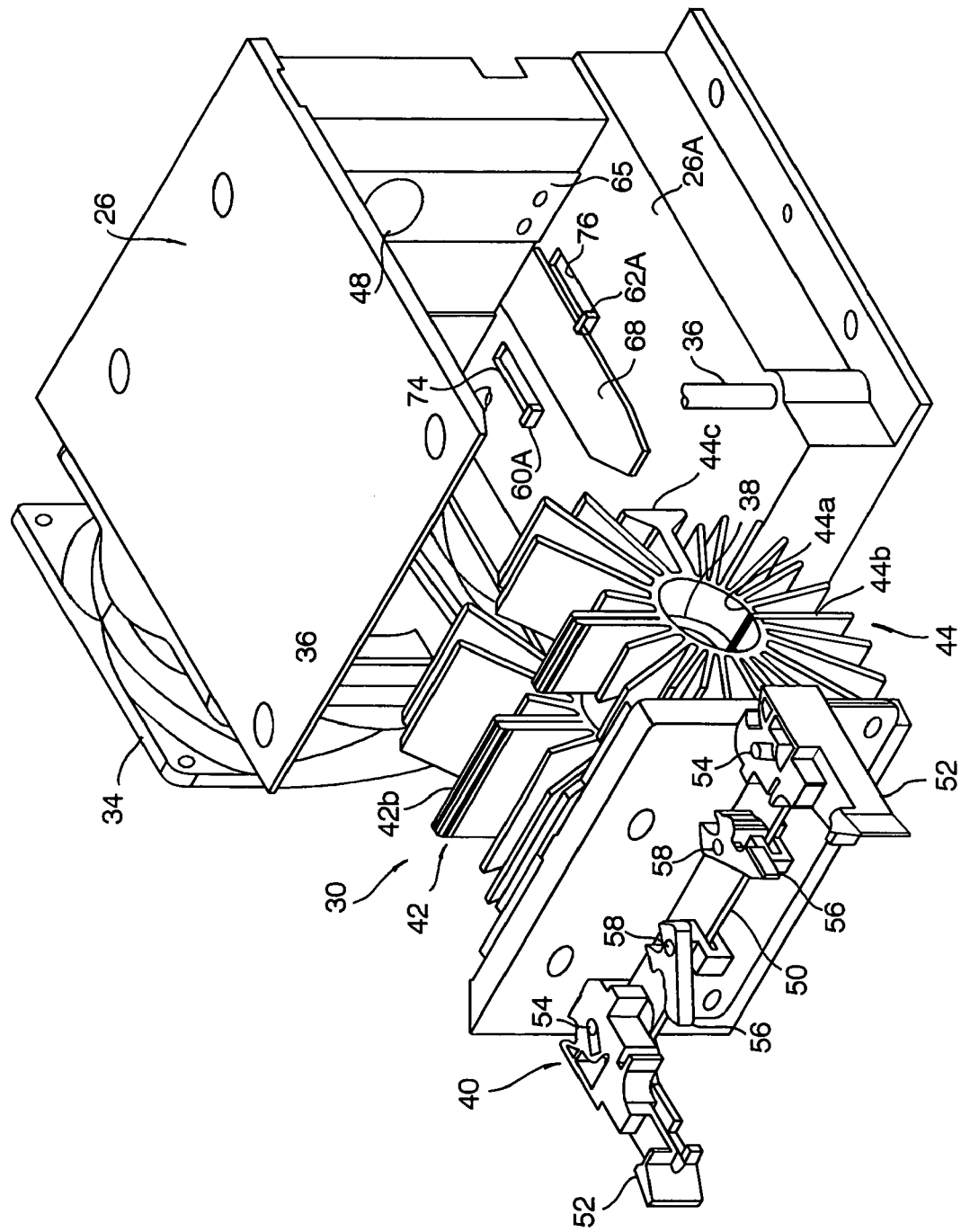
FIG. 3 is a perspective view of an internal structure of the light source device in which a light source unit is removed from a light source unit housing.
Figure 4:
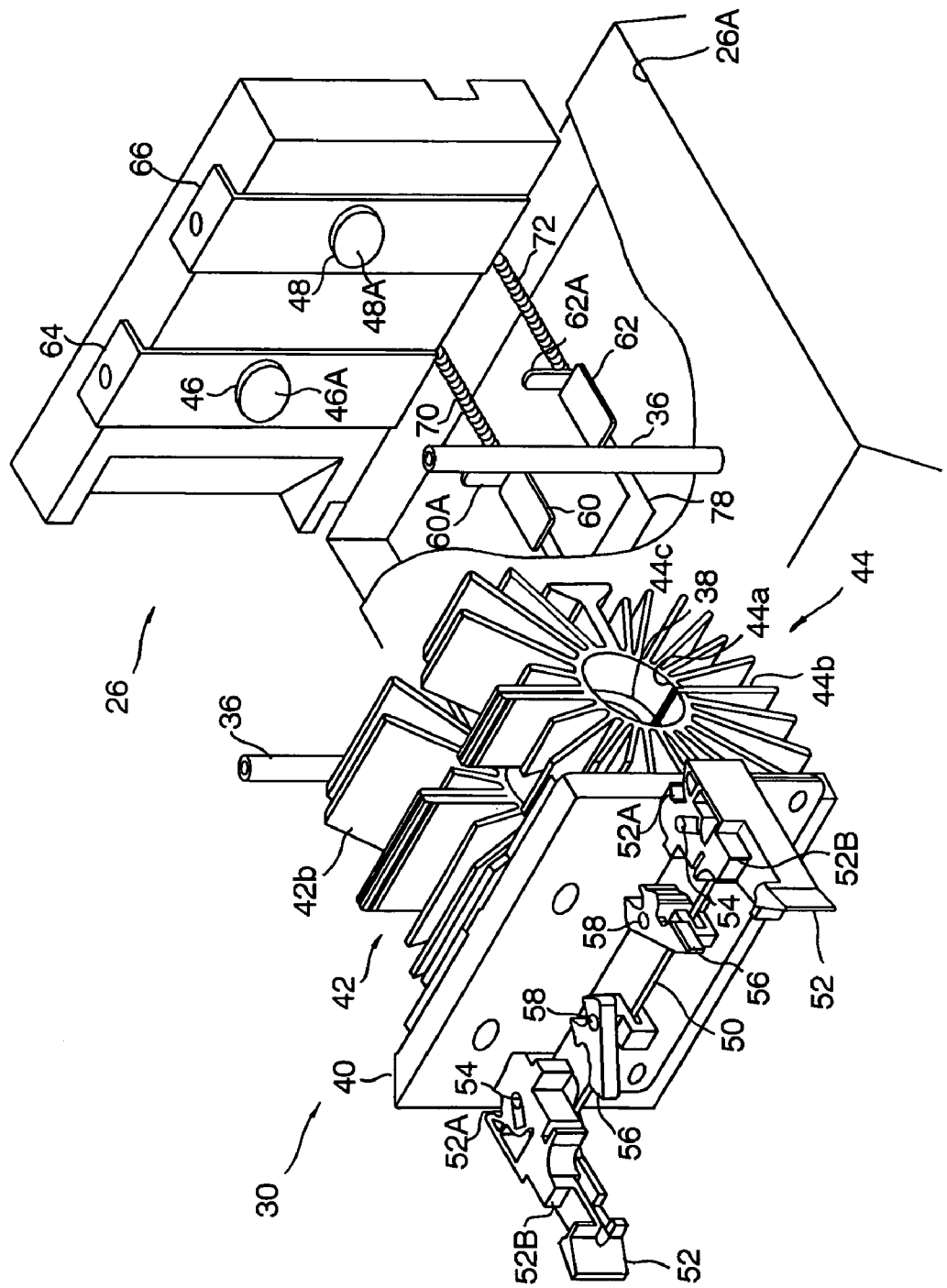
FIG. 4 is a perspective view of an internal structure of the light source device in which the light source unit housing is partly broken away.

Referring to FIGS. 3 through 6, the light source unit 30 is principally composed of a xenon lamp 38 as a light source, heat sinks 42 and 44, each serving as a socket having a socket bore 42a for the xenon lamp 38, a lamp mount board 40, an ejector bracket 50 available as a grip, a pair of ejectors 52 pivotally mounted on opposite extreme ends of the ejector bracket 50, and a pair of ejector locks 56 pivotally mounted cooperatively with the ejectors 52, respectively, on the ejector bracket 50. As shown in FIG. 4, the xenon lamp 38 is detachably held in the socket bores 42a of the heat sinks 42 and 44. The heat sinks 42 and 44, that are made of a good thermally and electrically conductive material such as aluminum or the like and electrically isolated, or otherwise separated by a distance, from each other, are provided with a number of radial fins 42b and 44b, respectively, so as to allow more efficient heat radiation. As will be described later, one of the fins of each of the heat sink is adapted to function as a second power electrode for the xenon lamp 38. The xenon lamp 38 is electrically connected to the heat sinks 42 and 44, namely the lamp socket, when held in position in the socket bores 42 of the heat sinks 42 and 44. As will be described later, the heat sinks 42 and 43, especially their associated electrode fins, are brought into contact with positive and negative first power electrodes 46 and 48 connected to a power supply circuit (not shown) through which electric power is supplied to the light source unit 30 and installed in the light source unit housing 26, respectively, when the light source unit 30 is set in position within the light source unit housing 26.

The lamp mount board 40 to which the heat sinks 42 and 44 are fixedly mounted is made of a low thermally conductive and electrically nonconductive material such as an epoxy resin and is shaped in form of a board. When the light source unit 30 is put in position within the light source unit housing 26, the lamp mount board 40 is located between cylindrical pillars 36 fixedly located within the light source unit housing 26 to serve as one of walls or a lid of the light source unit housing 26 so as to prevent an operator from accessing to the heat sinks 42 and 44 and/or the xenon lamp 38 within the light source unit housing 26. The ejector bracket 50 is fixedly attached to the lamp mount board 40 at the side remote from the heat sinks 42 and 44 and extends horizontally. The ejector bracket 50 at opposite extreme ends is provided with the ejectors 52 and 54, respectively. As clearly shown in FIG. 6, the ejector 52 is pivotally mounted on a pivot pin 54 vertically extending from the ejector bracket 50. The ejector 52 has a semi-circular catch recess 52A that is similar in shape to the cylindrical pillar 36 and capable of catching the cylindrical pillar 36 and a locking projection 52B. The ejector lock 56 is disposed adjacent to each of the ejectors 52 and pivotally mounted on a pivot pin 58 vertically extending from the ejector bracket 50. The ejector lock 56 has a locking recess 56B capable of engaging with the locking projection 52B of the ejector 52. When the ejector 52 is pivotally turned passing over the injector lock 56 in one direction and then returned halfway in the counter direction, the ejector 52 brings the locking projection 52B into engagement with the locking recess 56B of the ejector lock 56 to be locked in the turned position.

Figure 5A:
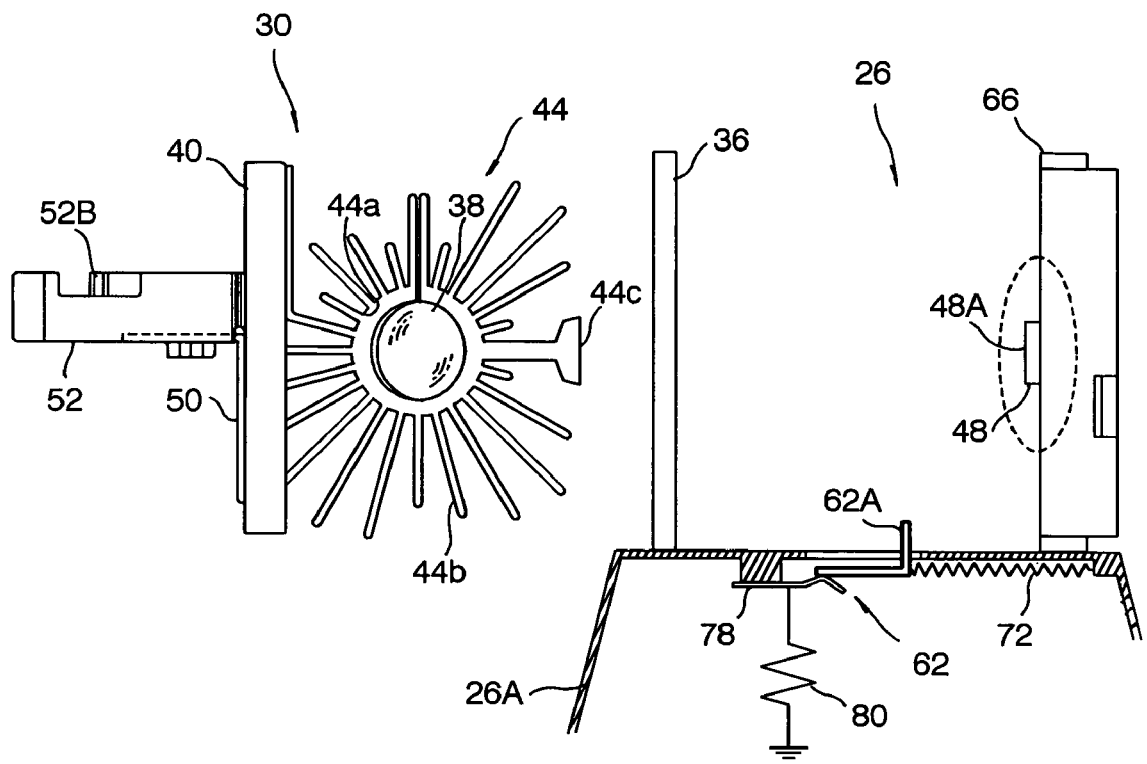
FIG. 5A is a schematic side view of the light source unit housing which is shown partly in cross section and the light source unit before insertion into the light source unit housing.
Figure 5B:
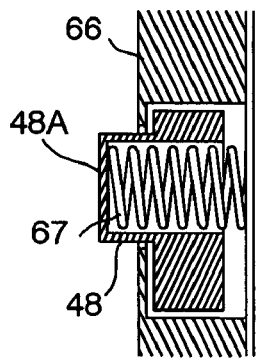
FIG. 5B is a cross sectional view of a first power electrode.
Figure 7A:
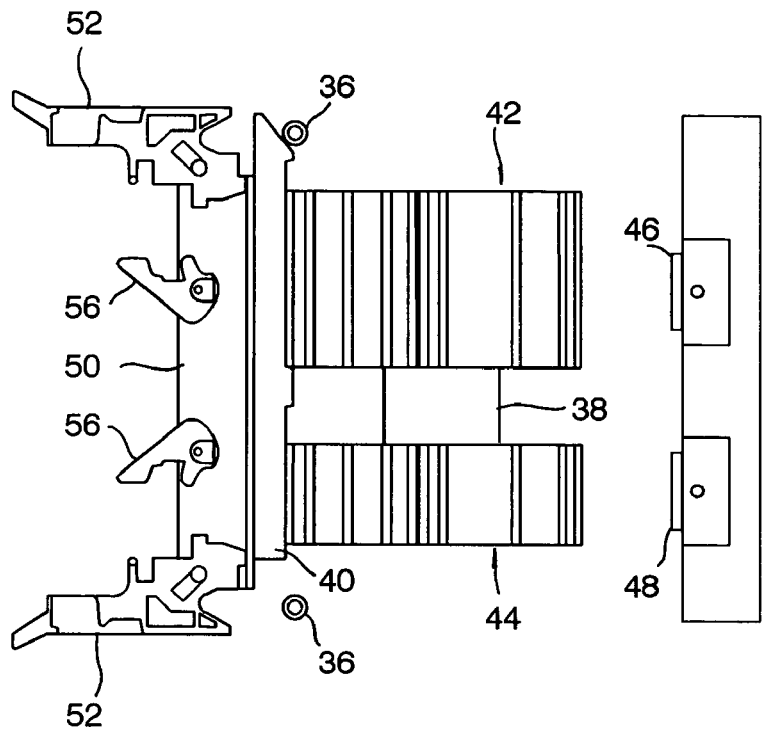
FIGS. 7A and 7B are a plane and a side view of the light source unit at the beginning of insertion into the light source unit housing, respectively.
Figure 7B:
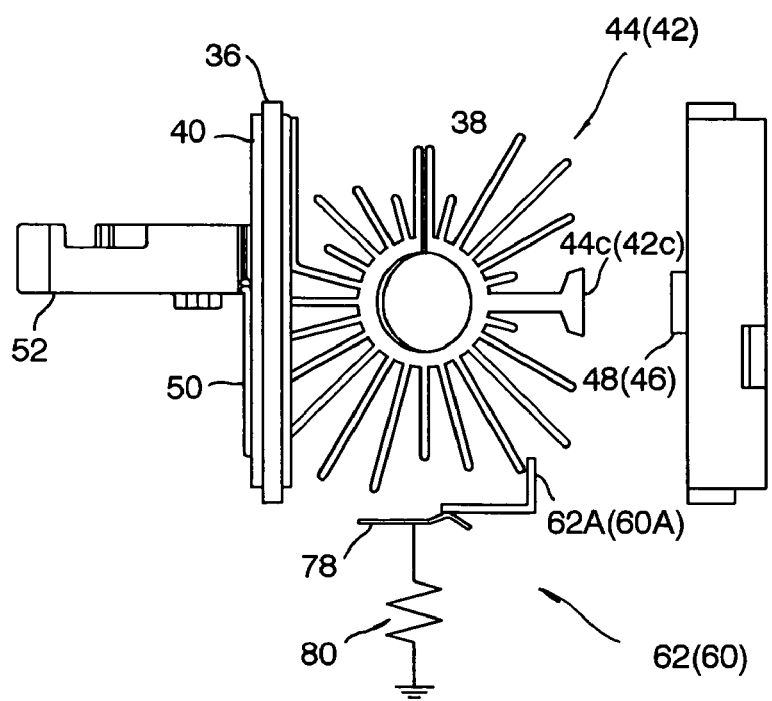

As shown in detail in FIGS. 4, 5A and 5B, the light source unit housing 26 is provided with the first power electrodes 46 and 48, a pair of sliding discharge electrodes 60 and 62 and a discharge circuit terminal 78. The first power electrode 48 is held by an electrode holder 66 for slide movement in directions of insertion and removal of the light source unit 30 with respect to the light source unit housing 26 (which are hereafter referred to as an insertion direction and a removal direction, respectively) and biased by bias means such as a biasing spring 67 in the removal direction so as to protrude from the electrode holder 66. Similarly, the first power electrode 46 is held by an electrode holder 64 for slide movement in both insertion and removal directions and biased in the removal direction by a biasing spring (not shown) so as to protrude from the electrode holder 64. When the light source unit 30 is inset in position within the light source unit housing 26, specific fins, that are adapted to function as a second power electrodes 42c and 44c, of the heat sinks 42 and 44 are brought into contact with contact surfaces 46A and 48A of the first power electrodes 46 and 48, respectively, held by the electrode holders 64 and 66, respectively, and push the electrodes 46 and 48 against the biasing springs 67, respectively. Even when the light source unit 30 is fully inserted into the light source unit housing 26, there is left a predetermined clearance between the electrodes 42c and 44c of the heat sinks 42 and 44 and the electrode holders 64 and 66, respectively.

As shown in detail in FIG. 5A, the sliding discharge electrode 60 has an upright tongue 60A and is supported for slide movement in both insertion and removal directions within a follow base 26A of the light source unit housing 26. Bias means such as a biasing spring 70 is mounted between the sliding discharge electrode 60 and the electrode holder 64 within the base 26A so as to bias the sliding discharge electrode 60 in the removal direction of the light source unit 30. The upright tongue 60A of the sliding discharge electrode 60 projects out of the base 26A through an opening 74 of the base 26A (see FIG. 3). Similarly, the sliding discharge electrode 62 has an upright tongue 62A and is supported for slide movement in both insertion and removal direction of the light source unit 30 within a follow base 26A of the light source unit housing 26. A biasing spring 72 is mounted between the sliding discharge electrode 62 and the electrode holder 66 within the base 12A so as to bias the sliding discharge electrode 62 in the removal direction of the light source unit 30. The upright tongue 62A of the sliding discharge electrode 62 projects out of the base 26A through an opening 76 of the base 26A (see FIG. 3). The sliding discharge electrodes 60 and 62 are forced against the biasing springs 70 and 71, respectively, by the radial fins 42b and 44b of the heat sink 42 and 44, respectively, when the light source unit 30 is inserted into the light source unit housing 26.

The discharge circuit terminal 78, that is generally U-shaped, is fixedly mounted within the base 26A of the light source unit light source unit housing 26 and grounded through a discharge circuit 80. The discharge circuit terminal 78 is so located that the sliding discharge electrodes 60A and 62A make slide contact with the discharge circuit terminal 78. More specifically, when the light source unit 30 is removed from the light source unit housing 26, the sliding discharge electrodes 60 and 62 are forced in the removal direction of the light source unit 30 by the biasing spring 70 and 72, respectively, to be brought into slide contact with the discharge circuit terminal 78. On the other hand, when the light source unit 30 is inserted into the light source unit housing 26, the sliding discharge electrodes 60 and 62 are forced in the insertion direction through the radial fins 42b and 44b, respectively, against the biasing spring 70 and 72, respectively, so as thereby to be separated from the discharge circuit terminal 78. The base 26A is provided with a guide plate 68 as shown in FIG. 3. The guide plate 68 has a width quite slightly smaller than the distance by which the heat sinks 42 and 44 are separated and guides movement of the light source unit 30, in particular the heat sinks 42 and 44, in both insertion and removal directions when the light source unit 30 is moved in the insertion and removal directions.

The following description will be directed to operation of the light source device 10 with reference to FIGS. 7 through 11. When the light source unit 30 is inserted into the light source unit housing 26, the door 14 is opened (see FIG. 1), and then the light source unit 30 is inserted through the access opening 12A and positioned between the pillars 36. As shown in FIGS. 7(A) and 7(B), at the beginning of insertion of the light source unit 30 into the light source unit housing 26, the radial fins 42b and 44b of the heat sink 42 and 44 are brought into contact with the upright tongues 60A and 62A of the sliding discharge electrodes 60 and 62, respectively. With further movement of the light source unit 30 in the insertion direction, the radial fins 42b and 44b of the heat sink 42 and 44 forces the upright tongues 60A and 62A to slide the sliding discharge electrodes 60 and 62, respectively, on the discharge circuit terminal 78 in the insertion direction and then to separate them from the discharge circuit terminal 78. The further continuous movement of the light source unit 30 for insertion of the light source unit 30 into the light source unit housing 26 brings the catch recesses 52A of the ejectors 52 to catch the pillars 36, respectively, as shown in FIGS. 8(A) and 8(B), and subsequently pivotally turns the ejectors 52 inwardly in opposite directions about the pivot pins 54, respectively, with their points of action at the pillars 36, respectively, as shown in FIG. 9(A).

Figure 10A:
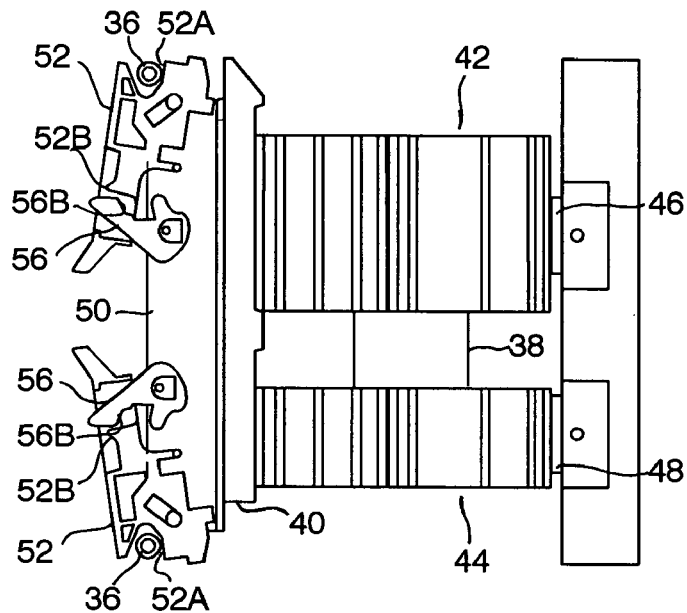
FIGS. 10A and 10B are a plane and a side view of the light source unit fully inserted in the light source unit housing, respectively.
Figure 10B:
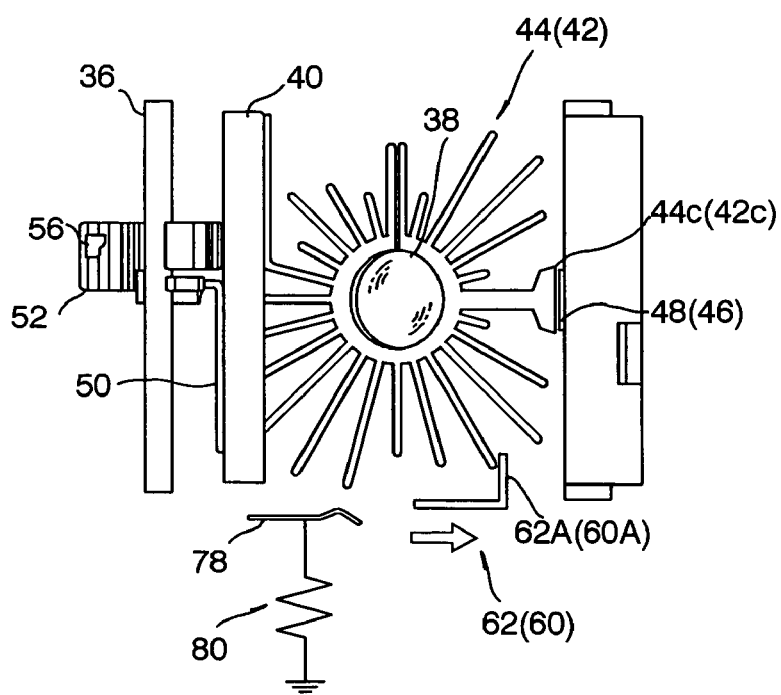
Figure 11A:
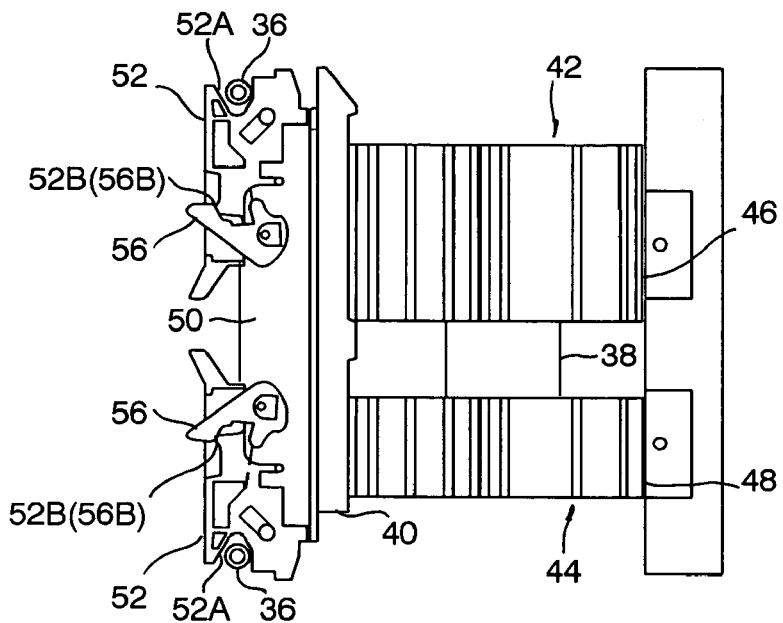
FIGS. 11A and 11B are a plane and a side view of the light source unit in which ejectors of the light source unit are locked, respectively.
Figure 11B:
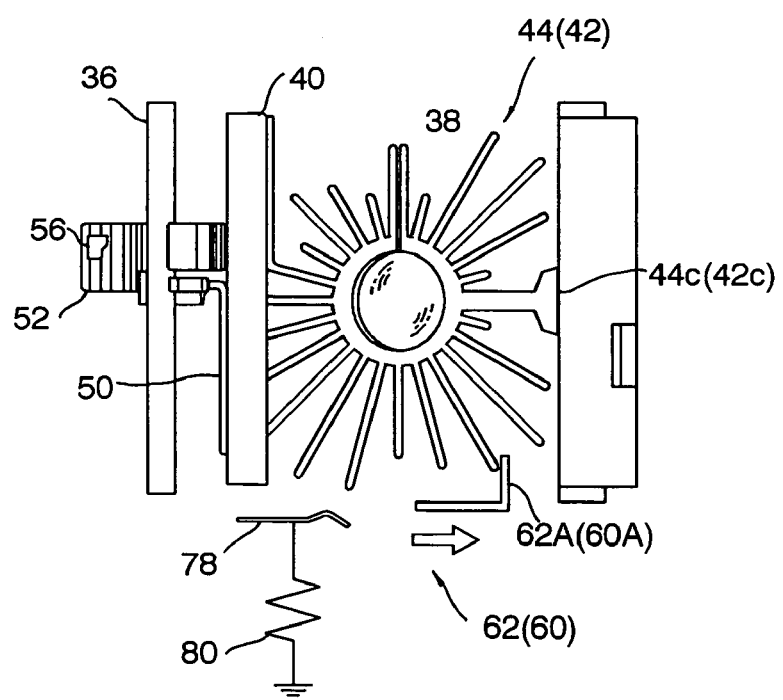

When the light source unit 30 is fully inserted into the light source unit housing 26, the electrodes 42c and 44c of the heat sink 42 and 44 come to contact with the counter electrodes 46 and 48, respectively, as shown in FIGS. 10(A) and 10(B). When the light source unit 30 is forcibly pushed in the insertion direction after the electrodes 42c and 44c of the heat sink 42 and 44 has been brought into contact with the counter electrodes 46 and 48, respectively, the electrodes 42c and 44c of the heat sink 42 and 44 forces the counter electrodes 46 and 48 against the biasing springs 67. At this time, the light source unit 30 further turns the ejectors 52 to thrust aside the associated ejector locks 52 outwardly in opposite directions and then allows them to turn back outwardly in opposite directions so as thereby to bring the locking projections 52B of the ejectors 52 into engagement with the locking recesses 56B of the ejector locks 56, respectively, as shown in FIGS. 11(A) and 11(B). As a result, each of the ejectors 52 is locked by the ejector lock 56. In this way, insertion of the light source unit 30 into the light source unit housing 26 is completed with the consequence that the electrodes 42c and 44c of the heat sink 42 and 44 are kept in close contact with the electrodes 64 and 66, respectively, under proper-contact pressure. Thereafter, when the door 14 is closed, the interlock release pin 20 is lead into the bore 22 of the case 12 to remove interlock between the xenon lamp 38 and the lighting unit 28 so as thereby to allow the xenon lamp 38 to be supplied electric power.

In the case where the light source unit 30 is incompletely inserted in the light source unit housing 26, or otherwise where the ejectors 52 are successively locked by the ejector locks 56, when the door 14 is turned toward the access opening 12A, then, the safety pins 24 strike on, for example, the ejectors 52, the ejector locks 56 or the ejector bracket 50, to hinder the door 14 from completely closing. Accordingly, the interlock release pin 20 is left out of the bore 22, thereby keeping electrical interlock between the xenon lamp 38 and the power source released. Therefore, the xenon lamp 38 is prevented from being excited while the door 14 is incompletely closed.

Figure 8A:
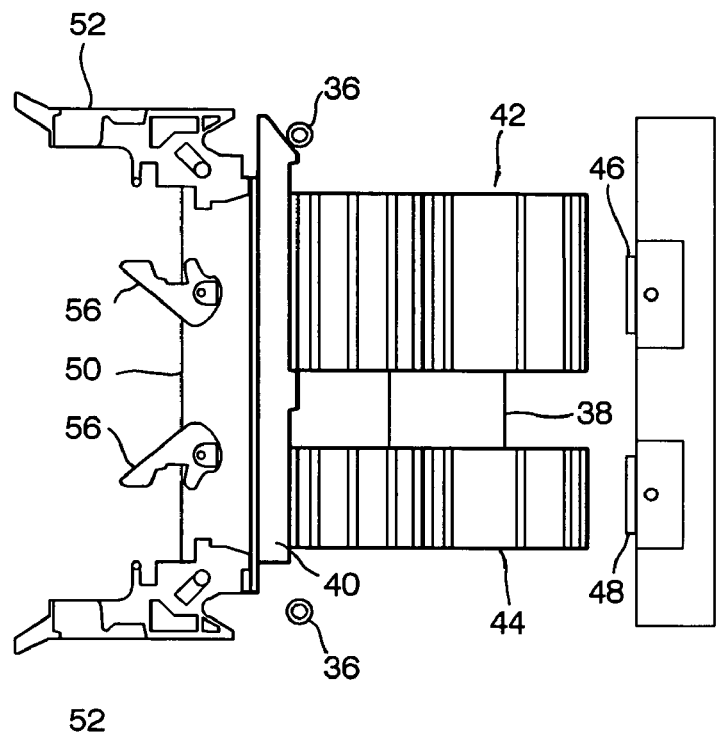
FIGS. 8A and 8B are a plane and a side view of the light source unit inserted to a halfway position in the light source unit housing where a sliding electrode is disconnected from a discharge circuit, respectively.
Figure 8B:
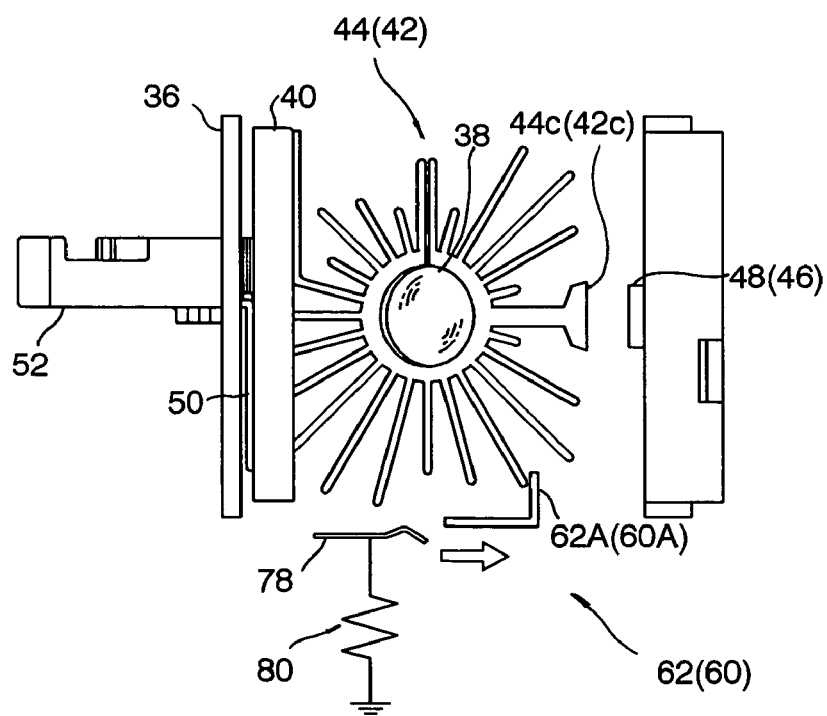
Figure 9A:
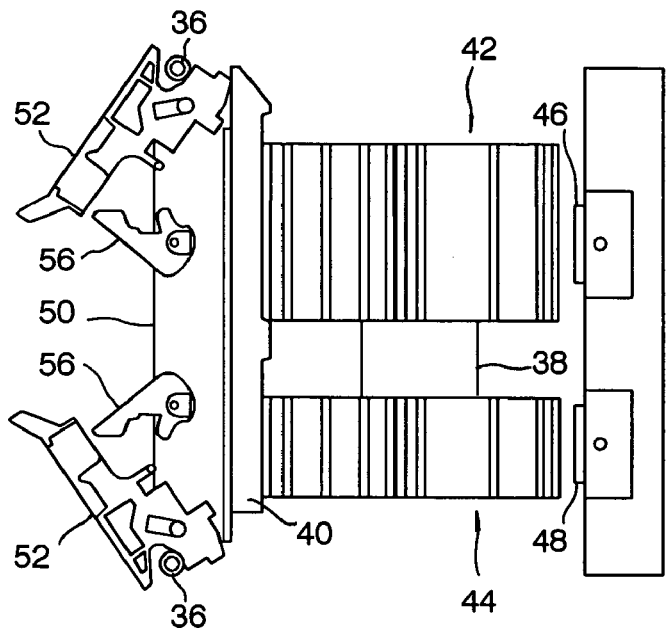
FIGS. 9A and 9B are a plane and a side view of the light source unit inserted closely to an end position in the light source unit housing, respectively.
Figure 9B:
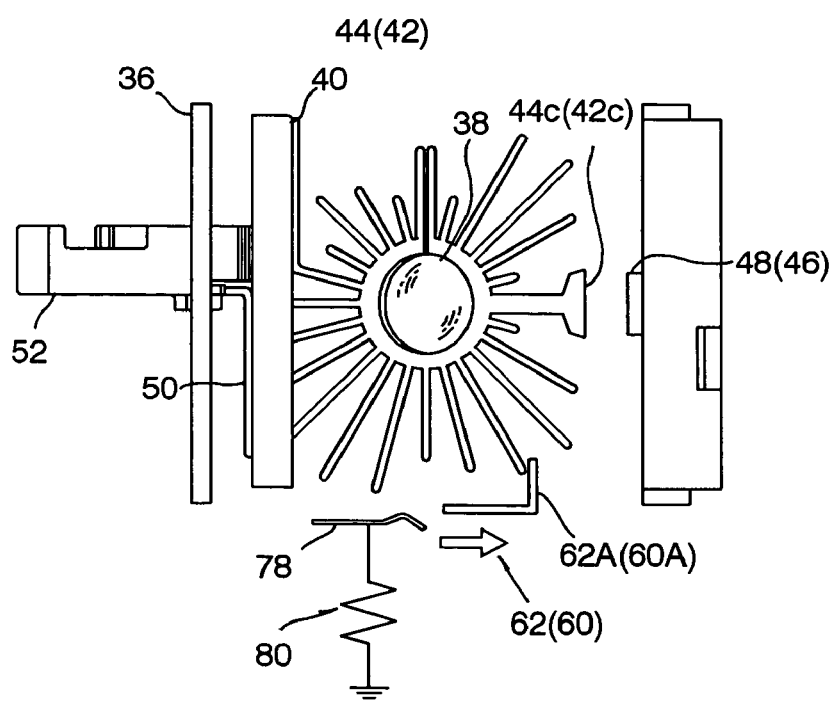

On the other hand, for removal of the light source unit 30 from the light source unit housing 26 for the purpose of, for example, replacement of lamps, the door 14 is opened. At this time, while the safety pins 24 are moved away from the ejectors 52 or the ejector locks 56, the interlock release pin 20 is pulled out of the bore 22 to release the electrical interlock between the xenon lamp 38 and the power source. Therefore, an access to the light source unit 30 or the xenon lamp 38 is safely allowed. After the door 14 is fully opened, the ejectors 56 are turned inwardly in opposite directions, respectively, to unlock the ejectors 52, respectively, as shown in FIG. 10(A). When the ejectors 52 are turned outwardly in opposite directions, respectively, about the pivot pins 54 with their points of reaction at the pillars 36, the light source unit 30 is pulled in the removal direction, thereby separating the electrodes 42c and 44c of the heat sink 42 and 44 away from the electrodes 46 and 48 of the light source unit housing 26, respectively as shown in FIGS. 9(A) and 9(B). At this time, the light source unit 30 is forced in the removal direction by the biasing springs 70 and 72 through the sliding discharge electrodes 60 and 62, turning the ejectors 52 is made quite easy. After completely erecting the ejectors 52 as shown in FIGS. 8(A) and 8(B), the ejector bracket 50 is grasped and pulled in the removal direction to pull the light source unit 30 fully out of the light source unit housing 26.

Since the ejector bracket 50 is attached to the heat sinks 42 and 44 through the lamp mount board 40 that is low in thermal conductivity, the ejector bracket 50 and the ejectors 52 are at a comparatively low temperature even in the case where the heat sinks 42 and 44 are still too hot to be caught by hand. Therefore, the operator can grasp the ejector bracket 50 safely and pull out the light source unit 30.

During further movement of the light source unit 30 in the removal direction, the sliding discharge electrodes 60 and 62 are brought into slide contact with the discharge circuit terminal 78 to discharge electric charges of the heat sinks 42 and 44 through the discharge circuit 80, thereby lowering electric potentials of the heat sinks 42 and 44 almost equally to that of the light source unit housing 26. The lamp mount board 40, that is electrically nonconductive, is positioned between the cylindrical pillars 36, preventing the operator from touching the heat sinks 42 and 44 before the heat sinks 42 and 44 have been discharged. In other words, when the light source unit is pulled out to a position where the heat sinks 42 and 44 can be touched by the operator, discharge of the heat sinks 42 and 44 have credibly been completed.

The present invention has been described with reference to preferred embodiments thereof. However, it will be appreciated that variants and other embodiments can be effected by person of ordinary skill in the art without departing from the scope of the invention.

The present invention has been described with reference to preferred embodiments thereof. However, it will be appreciated that variants and other embodiments can be effected by person of ordinary skill in the art without departing from the scope of the invention.

What is claimed is:

1. A light source device, comprising:
a light source unit housing;
a light source unit slidably mounted in the light source unit housing and including an electric lamp for supplying illumination light to an endoscope system, the electric lamp being electrically connected to a power source when the light source unit is inserted into the light source unit housing and disconnected from the power source when the light source unit is removed from the light source unit housing;
a pair of first power electrodes held for sliding movement in opposite directions for insertion and removal of the light source unit by the light source unit housing through which electric power is transmitted;
a pair of second power electrodes fixedly attached to the light source unit through which electric power is supplied to the electric lamp; and
biasing means incorporated in the light source unit housing for biasing the first power electrodes in the direction for removal;

a static electric discharge circuit incorporated in the light source unit housing that operates to discharge built-up electric charges;

sliding discharge electrodes forming part of the discharge circuit and held for slide movement in opposite directions for insertion and removal of the light source unit by the light source unit housing; and wherein, when the light source unit is inserted into the light source unit housing, the second power electrodes come to contact with and thrust back the first power electrodes against the biasing means, thereby electrically connecting the electric lamp to the power source.

2. A light source device as defined in claim 1, wherein the light source unit comprises a pair of heat sinks for radiating heat of the electric lamp which are arranged side by side with electric separation from each other so as to serve as a socket for receiving the electric lamp therein, each of the heat sinks having a plurality of radial fins one of which forms the second power electrode.

3. A light source device as defined in claim 2, wherein the light source unit comprises a lamp mount to which the heat sinks are fixedly mounted, the lamp mount being made of a material that is electrically nonconductive and low in thermal conductivity.

4. A light source device as defined in claim 1, and further comprising an outer case with an access opening to the light source unit inserted in the light source unit housing, a door for opening and closing the access opening and safety means fixedly attached to an inner side of the door for preventing the door from closing the access opening when the light source unit is in a false position in the light source unit housing.

5. A light source device as defined in claim 4, wherein the safety means comprises a pin that is brought into a strike on the light source unit when the light source unit is in a false position in the light source unit housing.

6. A light source device as defined in claim 4, and further comprising interlock release means fixedly attached to the inner side of the door, wherein the interlock release means electrically interlocks the power source and the electric lamp when the door is closed and releases electric interlock between the power source and the electric lamp when the door is opened.

7. A light source device having a light source unit housing and a light source unit including an electric lamp for supplying illumination light to an endoscope system, the electric lamp being electrically connected to a power source when the light source unit is inserted into the light source unit housing and disconnected from the power source when the light source unit is removed from the light source unit housing, the light source device comprising:

socket means fixedly incorporated in the light source unit for receiving the electric lamp;

a discharge circuit incorporated in the light source unit housing that operates to discharge electric charges built up in an object when electrically connected to the charge built-up object;

sliding discharge electrodes forming part of the discharge circuit and held for slide movement in opposite directions for insertion and removal of the light source unit by the light source unit housing; and biasing means for biasing the sliding discharge electrodes in the direction for removal of the light source unit so as thereby to keep the sliding discharge electrodes connected to the discharge circuit;

wherein the light source unit forces the sliding discharge electrodes against the biasing means through engagement between the socket means and the sliding discharge electrodes so as to electrically disconnect the sliding discharge electrodes from the discharge circuit following movement of the light source unit in the direction for insertion into the light source unit housing and allows the sliding discharge electrodes to slide keeping in contact with the socket means and to be brought into electric connection with the discharge circuit following movement of the light source unit in the direction for removal from the light source unit housing so as thereby to electrically connect the socket means as the charge built-up object with the discharge circuit.

8. A light source device as defined in claim 7, wherein the socket comprises a pair of heat sinks for radiating heat of the electric lamp which are arranged side by side with electric separation from each other, each of the heat sinks having a socket bore for receiving the electric lamp therein and a plurality of radial fins one of which is engageable with the sliding discharge electrode.

9. A light source device as defined in claim 8, and further comprising a lamp mount for fixedly mounting the heat sinks thereto, wherein the lamp mount is made of a material that is electrically nonconductive and low in thermal conductivity.

10. A light source device as defined in claim 7, and further comprising an outer case with an access opening to the light source unit inserted in the light source unit housing, a door for opening and closing the access opening and safety means fixedly attached to an inner side of the door, wherein the safety means is brought into a strike on the light source unit so as thereby to prevent the door from closing the access opening when the light source unit is in a false position in the light source unit housing.

11. A light source device as defined in claim 10, wherein the safety means comprises a pin that is brought into a strike on the light source unit when the light source unit is in a false position in the light source unit housing.

12. A light source device as defined in claim 10, and further comprising interlock release means fixedly attached to the inner side of the door, wherein the interlock means electrically interlocks the power source and the electric lamp when the door is closed and releases electric interlock between the power source and the electric lamp when the door is opened.

13. A light source device having a light source unit housing and a light source unit including an electric lamp for supplying illumination light, the light source unit is removably inserted into the light source unit housing, the light source device comprising:

an outer casing with an access opening to the light source unit inserted in the light source unit housing;

a door for opening and closing the access opening;

a discharge circuit incorporated in the light source unit housing that operates to discharge built-up electric charges;

sliding discharge electrodes forming part of the discharge circuit and held for slide movement in opposite directions for insertion and removal of the light source unit by the light source unit housing;

biasing means for biasing the sliding discharge electrodes in the direction for removal of the light source unit so as thereby to keep the sliding discharge electrodes connected to the discharge circuit; and safety means fixedly attached to an inner side of the door for preventing the door from closing the access opening when the light source unit is in a false position in the light source unit housing.

14. A light source device, comprising:
a case (12) with an access opening (12A)
a door (14) for opening and closing the access opening;
a slidingly removable light source unit (30) exposed through the access opening and configured for receiving a lamp (38)
first power electrodes (46, 48) for energizing the light source unit by sliding contact the light source unit;
a discharge circuit connected to discharge built-up static electricity upon removal of the light source unit from within the case through the access opening, the discharge circuit comprising a pair of spring-biased, sliding discharge electrodes (60, 62) and a discharge circuit terminal (78) connectable intermediate each electrode of the pair of discharge electrodes, upon removal of the light source unit and sliding movement of the discharge electrodes.

15. The device of claim 14, wherein,
the first power electrodes are spring biased in a direction of insertion and a direction of removal of the light source unit,
the discharge circuit terminal connects to ground, and
the light source unit comprising heat sink fins adapted as second power electrodes slidable into contact with contact surfaces of the first power electrodes.

16. The device of claim 15, wherein,
the discharge circuit terminal is fixedly mounted and sliding movement of the discharge electrodes makes contact with the discharge circuit terminal to ground the light source unit and discharge the static electricity.

\* \* \* \* \*